United States Patent [19]

Bartmann et al.

[11] Patent Number: 5,045,229
[45] Date of Patent: Sep. 3, 1991

[54] DIFLUOROMETHYLENE COMPOUNDS

[75] Inventors: Ekkehard Bartmann, Erzhausen; Reinhard Hittich, Modautal; Hans-Adolf Kurmeier, Seeheim-Jugenheim; Eike Poetsch, Mühltal; Herbert Plach, Darmstadt, all of Fed. Rep. of Germany

[73] Assignee: Merck Patent Gesellschaft mit Beschrankter Haftung, Darmstadt, Fed. Rep. of Germany

[21] Appl. No.: 494,372

[22] Filed: Mar. 16, 1990

[30] Foreign Application Priority Data

Mar. 18, 1989 [DE] Fed. Rep. of Germany ....... 3908945

[51] Int. Cl.$^5$ ..................... C09K 19/34; C09K 19/30; G02F 1/13; C07C 22/00
[52] U.S. Cl. .......................... 252/299.01; 252/299.61; 252/299.63; 252/299.66; 252/299.65; 359/103; 560/65; 560/100; 560/64; 568/18; 568/23; 568/74; 568/327; 549/373; 585/23; 570/144; 570/128; 570/129
[58] Field of Search .................... 350/350 R; 570/129, 570/131, 144, 128; 252/299.63, 299.64, 299.01, 229.61, 299.65, 299.66; 560/64, 65, 100; 568/23, 24, 302, 327, 328, 18, 74; 558/303; 546/184, 186, 268; 544/360, 370; 549/378; 585/23

[56] References Cited

U.S. PATENT DOCUMENTS

| | | | |
|---|---|---|---|
| 4,330,426 | 5/1982 | Eidenschink et al. | 252/299.63 |
| 4,536,321 | 8/1985 | Sugimori | 252/299.63 |
| 4,886,619 | 1/1989 | Janulis | 252/299.1 |
| 4,915,480 | 4/1990 | Petrzilka et al. | 350/350 R |

FOREIGN PATENT DOCUMENTS

| | | | |
|---|---|---|---|
| 041682 | 12/1981 | European Pat. Off. | 568/306 |
| 0272580 | 6/1988 | European Pat. Off. | 568/306 |

OTHER PUBLICATIONS

V. V. Titov et al., "Synthesis and Mesomorphism of Aryl P-Fluoralkyl-(alkoxy)benzoates", *Mol. Cryst. Liq. Cryst.*, 47:1–5, 1978.

S. V. Sereda et al., Kristallografiya 32, 1165–1174, 1987.

*Primary Examiner*—Robert L. Stoll
*Assistant Examiner*—C. Harris
*Attorney, Agent, or Firm*—Millen, White & Zelano

[57] ABSTRACT

Difluoromethylene compounds of the formula I

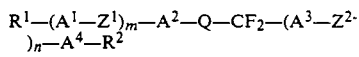

$$R^1-(A^1-Z^1)_m-A^2-Q-CF_2-(A^3-Z^2)_n-A^4-R^2 \qquad I$$

in which $R^1$, $R^2$, $A^1$, $A^2$, $A^3$, $A^4$, $Z^1$, $Z^2$, m and n are as defined herein and Q is —CO—, —O— or —S—, can be used as components of liquid-crystalline media for liquid-crystal and electrooptical display elements.

16 Claims, No Drawings

DIFLUOROMETHYLENE COMPOUNDS

SUMMARY OF THE INVENTION

The invention relates to difluoromethylene compounds of the formula I

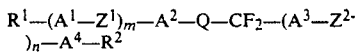

$$R^1-(A^1-Z^1)_m-A^2-Q-CF_2-(A^3-Z^2-)_n-A^4-R^2 \quad I$$

in which $R^1$ and $R^2$, in each case independently of one another, are an alkyl or alkenyl radical having 1 to 15 C atoms which is in each case unsubstituted, monosubstituted by CN or $CF_3$ or at least monosubstituted by halogen, it also being possible in these radicals for one or two $CH_2$ groups, in each case independently of one another, to be replaced by —O—,

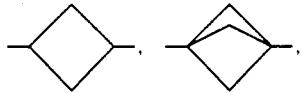

—CO—, —CO—O—, —O—CO— or —O—CO—O— in a manner such that O atoms are not linked directly to one another, and one of the radicals $R^1$ and $R^2$ may alternatively be H, halogen, —CN or —NCS, $A^1$, $A^2$ and $A^3$, in each case independently of one another, are a (a) trans-1,4-cyclohexylene radical in which, in addition, one or two non-adjacent $CH_2$ groups may be replaced by —O— and/or —S—, (b) 1,4-phenylene radical, in which, in addition, one or two CH groups may be replaced by N, (c) radical from the group comprising 1,4-cyclohexenylene, 1,3-cyclobutylene, 1,4-bicyclo(2,2,2)octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) may be substituted by one CN or up to four fluorine, $A^4$ has one of the definitions of $A^1$, $A^2$ and $A^3$ or, in the case where n=0, is alternatively a single bond, $Z^1$ and $Z^2$, in each case independently of one another, are —CO—O—, —O—CO—, —CH$_2$O—, —OCH$_2$—, —CH$_2$CH$_2$—, —CH=CH—, —C≡C— or a single bond, m is 1, 2 or 3, n is 0, 1 or 2, and Q is —CO—, —O— or —S—, with the provisos that (a) (m+n) is 1, 2 or 3, (b) $R^2$ is chlorine or —CN if n=0, Q=O and $A^4$ is a single bond, (c) $R^2$ is halogen or —CN if n=0, Q is S and $A^4$ is a single bond, and (d) $R^2$ is H, halogen or —CN if n=0, Q=CO and $A^4$ is a single bond.

The invention furthermore relates to the use of these compounds as components of liquid crystalline media, and to liquid-crystal and electrooptical display elements which contain the liquid-crystalline media according to the invention.

The compounds of the formula I can be used as components of liquid-crystalline media, in particular for displays based on the principle of the twisted cell, including highly twisted variants thereof, such as, for example, STN or SBE, the guest-host effect, the effect of deformation of aligned phases or the effect of dynamic scattering.

The invention has an object of finding novel stable liquid-crystalline or mesogenic compounds which are suitable as components of liquid-crystalline media and in particular have comparatively low viscosity and a moderate positive dielectric anisotropy.

It has now been found that compounds of the formula I are pre-eminently suitable as components of liquid-crystalline phases. In particular, they have comparatively low viscosities. Using them, stable liquid-crystalline phases which have a broad mesophase range, advantageous values for the optical and dielectric anisotropy and are at the same time distinguished by very favorable values for the specific resistance can be obtained. This gives considerable advantages, in particular in the case of media for active matrix displays or supertwist displays.

Similar compounds having liquid-crystalline properties and one terminal $OCHF_2$ group have already been disclosed. On the one hand, crystal structure studies have been carried out on appropriate compounds [S. V. Sereda et al. in Kristallografiya, 32 (5), 1165 (1987) and ibid. 33 (1) 118 (1988)]. In contrast to the compounds according to the invention, however, these compounds contain nitrogen-containing bridging members. On the other hand, V. V. Titov et al. in Mol. Cryst. Liq. Cryst. 47 (1–2), 1 (1978) have described benzoic acid esters with an $OCHF_2$ group in the p-position. However, they generally have comparatively disadvantageous values for the dielectric anisotropy and are significantly inferior to the compounds according to the invention for modern display applications.

In addition, the provision of the compounds of the formula I very generally considerably extends the range of liquid-crystalline substances which are suitable, from various applicational points of view, for the preparation of liquid-crystalline mixtures.

The compounds of the formula I have a broad field of application. Depending on the choice of substituents, these compounds can be used as base materials from which liquid-crystalline phases are predominantly composed; however, compounds of the formula I can also be added to liquid-crystalline base materials from other classes of compounds, in order, for example, to influence the dielectric and/or optical anisotropy of a dielectric of this type and/or to optimize its threshold voltage and/or its viscosity.

In the pure state, the compounds of the formula I are colorless and form liquid-crystalline mesophases in a very favorable temperature range for electrooptical use. They are stable chemically, thermally and to light.

The invention also relates to the compounds of the formula I, in particular compounds of the formula I1,

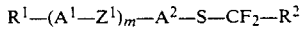

$$R^1-(A^1-Z^1)_m-A^2-S-CF_2-R^2 \quad I1$$

in which $R^1$, $A^1$, $Z^1$, m and $A^2$ are as defined above and $R^2$ is fluorine, chlorine or —CN, of the formula I2,

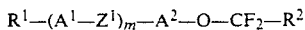

$$R^1-(A^1-Z^1)_m-A^2-O-CF_2-R^2 \quad I2$$

in which $R^2$, $R^1$, $Z^1$, m and $A^2$ are as defined above and $R^2$ is —CN or chlorine, and of the formula I3

$R^1-(A^1-Z^1)_m-A^2-CO-CF_2-R^2$  I3 in which $R^1$, $A^1$, $Z^1$, m and $A^2$ are as defined above and $R^2$ is H, fluorine, chlorine or —CN.

The invention furthermore relates to the use of these compounds as components of liquid-crystalline media. The invention furthermore relates to liquid-crystalline media containing at least one compound of the formula I, and to liquid-crystal display elements, in particular electrooptical display elements, which contain media of this type.

For reason of simplicity, X below is —Q—$CF_2$—, Cyc is a 1,4-cyclohexylene radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical and Bi is a bicyclo(2,2,2)octylene radical, where Cyc and/or Phe may be unsubstituted or monosubstituted or disubstituted by F or CN.

Accordingly, the compounds of the formula I include compounds, having two rings, of the sub-formulae Ia to Ic:

$R^1-A^1-A^2-X-R^2$  Ia $R^1-A^1-Z^1-A^2-X-R^2$  Ib $R^1-A^2-X-A^4-R^2$  Ic compounds having three rings, of the sub-formulae Id to Ik:

$R^1-A^1-A^1-A^2-X-R^2$  Id $R^1-A^1-Z^1-A^1-Z^1-A^2-X-R^2$  Ie $R^1-A^1-Z^1-A^1-A^2-X-R^2$  If $R^1-A^1-A^1-Z^1-A^2-X-R^2$  Ig $R^1-A^1-X-A^3-A^4-R^2$  Ih $R^1-A^1-A^2-X-A^4-R^2$  Ii $R^1-A^2-X-A^3-Z^2-A^4-R^2$  Ij $R^1-A^1-Z^1-A^2-X-A^4-R^2$  Ik and compounds having four rings, of the sub-formulae Il to Iy:

$R^1-A^1-A^1-A^1-A^2-X-R^2$  Il $R^1-A^1-Z^1-A^1-A^1-A^2-X-R^2$  Im $R^1-A^1-A^1-Z^1-A^1-A^2-X-R^2$  In $R^1-A^1-A^1-A^1-Z-A^2-X-R^2$  Io $R^1-A^1-Z^1-A^1-Z^1-A^1-A^2-X-R^2$  Ip $R^1-A^1-Z^1-A^1-A^1-Z^1-A^2-X-R^2$  Iq $R^1-A^1-A^1-Z^1-A^1-Z^1-A^2-X-R^2$  Ir $R^1-A^1-Z^1-A^1-Z^1-A^1-Z^2-A^2-X-R^2$  Is $R^1-A^1-A^1-A^2-X-A^4-R^2$  It $R^1-A^1-A^2-X-A^3-A^4-R^2$  Iu $R^1-A^2-X-A^3-A^3-A^4-R^2$  Iv $R^1-A^1-Z^1-A^1-A^2-X-A^4-R^2$  Iw $R^1-A^1-A^1-Z^1-A^2-X-A^4-R^2$  Ix $R^1-A^1-Z^1-A^2-X-A^3-A^4-R^2$  Iy

Of these, those of the sub-formulae Ia, Ib, Ic, Id, Ie, If, Ig, Ih, Ii and Il are particularly preferred.

The preferred compounds of the sub-formula Ia include those of the sub-formulae Iaa to Iah:

$R^1-Phe-Phe-X-R^2$  Iaa $R^1-Phe-Cyc-X-R^2$  Iab $R^1-Dio-Phe-X-R^2$  Iac $R^1-Pyr-Phe-X-R^2$  Iad $R^1-Pyd-Phe-X-R^2$  Iae $R^1-Cyc-Phe-X-R^2$  Iaf $R^1-Cyc-Cyc-X-R^2$  Iag $R^1-Che-Phe-X-R^2$  Iah

Of these, those of the formulae Iaa, Iab, Iac, Iad, Iaf and Iag are particularly preferred.

The preferred compounds of the sub-formula Ib include those of the sub-formulae Iba to Ibm:

$R^1-Phe-CH_2CH_2-Phe-X-R^2$  Iba $R^1-Phe-OCH_2-Phe-X-R^2$  Ibb $R^1-Cyc-CH_2CH_2-Phe-X-R^2$  Ibc $R^1-Cyc-CH_2-CH_2-Cyc-X-R^2$  Ibd $R^1-Cyc-COO-Phe-X-R^2$  Ibe $R^1-Cyc-COO-Cyc-X-R^2$  Ibf $R^1-A^1-CH_2CH_2-Phe-X-R^2$  Ibg $R^1-A^1-CH_2CH_2-Cyc-X-R^2$  Ibh $R^1-A^1-CH_2O-Phe-X-R^2$  Ibi $R^1-A^1-OCH_2-Phe-X-R^2$  Ibj $R^1-A^1-COO-Phe-X-R^2$  Ibk $R^1-A^1-OCO-Phe-X-R^2$  Ibl $R^1-Che-CH_2CH_2-Phe-X-R^2$  Ibm

The preferred compounds of the sub-formula Ic include those of the sub-formulae Ica to Icd:

$R^1-Phe-X-Phe-R^2$  Ica $R^1-Cyc-X-Phe-R^2$  Icb $R^1-Phe-X-Cyc-R^2$  Icc $R^1-Cyc-X-Cyc-R^2$  Icd

The preferred compounds of the sub-formula Id include those of the sub-formulae Ida to Idm:

| | |
|---|---|
| R¹—Phe—Phe—Phe—X—R² | Ida |
| R¹—Phe—Phe—Cyc—X—R² | Idb |
| R¹—Phe—Dio—Phe—X—R² | Idc |
| R¹—Cyc—Cyc—Phe—X—R² | Idd |
| R¹—Cyc—Cyc—Cyc—X—R² | Ide |
| R¹—Pyd—Phe—Phe—X—R² | Idf |
| R¹—Pyr—Phe—Phe—X—R² | Idg |
| R¹—Phe—Pyr—Phe—X—R² | Idh |
| R¹—Cyc—Phe—Phe—X—R² | Idi |
| R¹—Cyc—Phe—Cyc—X—R² | Idj |
| R¹—Dio—Phe—Phe—X—R² | Idk |
| R¹—Che—Phe—Phe—X—R² | Idl |
| R¹—Phe—Che—Phe—X—R² | Idm |

Of these, those of the formulae Ida, Idc, Idd, Ide, Idi and Idj are particularly preferred.

The preferred compounds of the sub-formula Ie include those of the sub-formulae Iea to Iem:

| | |
|---|---|
| R¹—Phe—Z¹—Phe—Z¹—Phe—X—R² | Iea |
| R¹—Phe—Z¹—Phe—Z¹—Cyc—X—R² | Ieb |
| R¹—Phe—Z¹—Dio—Z¹—Phe—X—R² | Iec |
| R¹—Cyc—Z¹—Cyc—Z¹—Phe—X—R² | Ied |
| R¹—Cyc—Z¹—Cyc—Z¹—Cyc—X—R² | Iee |
| R¹—Pyd—Z¹—Phe—Z¹—Phe—X—R² | Ief |
| R¹—Phe—Z¹—Pyd—Z¹—Phe—X—R² | Ieg |
| R¹—Pyr—Z¹—Phe—Z¹—Phe—X—R² | Ieh |
| R¹—Phe—Z¹—Pyr—Z¹—Phe—X—R² | Iei |
| R¹—Phe—Z¹—Cyc—Z¹—Phe—X—R² | Iej |
| R¹—Cyc—Z¹—Phe—Z¹—Cyc—X—R² | Iek |
| R¹—Dio—Z¹—Phe—Z¹—Phe—X—R² | Iel |
| R¹—Che—Z¹—Phe—Z¹—Phe—X—R² | Iem |

The preferred compounds of the sub-formula If include those of the sub-formulae Ifa to Ifk:

| | |
|---|---|
| R¹—Pyr—Z¹—Phe—Phe—X—R² | Ifa |
| R¹—Dio—Z¹—Phe—Phe—X—R² | Ifb |
| R¹—Cyc—Z¹—Phe—Phe—X—R² | Ifc |
| R¹—Cyc—Z¹—Phe—Cyc—X—R² | Ifd |
| R¹—Phe—Z¹—Cyc—Phe—X—R² | Ife |
| R¹—Cyc—Z¹—Cyc—Phe—X—R² | Iff |
| R¹—Cyc—Z¹—Cyc—Cyc—X—R² | Ifg |
| R¹—Phe—Z¹—Dio—Phe—X—R² | Ifh |
| R¹—Pyd—Z¹—Phe—Phe—X—R² | Ifi |
| R¹—Phe—Z¹—Pyr—Phe—X—R² | Ifj |
| R¹—Phe—Z¹—Che—Phe—X—R² | Ifk |

The preferred compounds of the sub-formula Ig include those of the sub-formulae Iga to Igp:

| | |
|---|---|
| R¹—Pyr—Phe—Z¹—Phe—X—R² | Iga |
| R¹—Pyr—Phe—OCH₂—Phe—X—R² | Igb |
| R¹—Phe—Phe—Z¹—Phe—X—R² | Igc |
| R¹—Phe—Phe—Z¹—Cyc—X—R² | Igd |
| R¹—Cyc—Cyc—Z¹—Phe—X—R² | Ige |
| R¹—Cyc—Cyc—Z¹—Cyc—X—R² | Igf |
| R¹—Cyc—Cyc—CH₂CH₂—Phe—X—R² | Igg |
| R¹—Pyd—Phe—Z¹—Phe—X—R² | Igh |
| R¹—Dio—Phe—Z¹—Phe—X—R² | Igi |
| R¹—Phe—Cyc—Z¹—Phe—X—R² | Igj |
| R¹—Phe—Cyc—Z¹—Cyc—X—R² | Igk |
| R¹—Phe—Pyd—Z¹—Phe—X—R² | Igl |
| R¹—Che—Phe—Z¹—Phe—X—R² | Igm |
| R¹—Phe—Che—Z¹—Phe—X—R² | Ign |
| R¹—Cyc—Phe—Z¹—Phe—X—R² | Igo |
| R¹—Cyc—Phe—Z¹—Cyc—X—R² | Igp |

The preferred compounds of the sub-formula Ih include those of the sub-formulae Iha to Ihh:

| | |
|---|---|
| R¹—Phe—X—Phe—Phe—R² | Iha |
| R¹—Phe—X—Cyc—Phe—R² | Ihb |
| R¹—Phe—X—Cyc—Cyc—R² | Ihc |
| R¹—Phe—X—Phe—Cyc—R² | Ihd |
| R¹—Cyc—X—Phe—Cyc—R² | Ihe |
| R¹—Cyc—X—Phe—Phe—R² | Ihf |
| R¹—Cyc—X—Cyc—Phe—R² | Ihg |
| R¹—Cyc—X—Cyc—Cyc—R² | Ihh |

The preferred compounds of the sub-formula Ii include those of the sub-formulae Iia to Iih:

| | |
|---|---|
| R¹—Phe—Phe—X—Phe—R² | Iia |
| R¹—Phe—Phe—X—Cyc—R² | Iib |
| R¹—Phe—Cyc—X—Cyc—R² | Iic |
| R¹—Phe—Cyc—X—Phe—R² | Iid |

R¹—Cyc—Cyc—X—Phe—R²    IIe

R¹—Cyc—Cyc—X—Cyc—R²    IIf

R¹—Cyc—Phe—X—Cyc—R²    IIg

R¹—Cyc—Phe—X—Phe—R²    IIh

The preferred compounds of the formula II include those of the formula IIa to IIf:

R¹—Phe—Phe—Phe—X—R²    IIa

R¹—Cyc—Phe—Phe—Phe—X—R²    IIb

R¹—Cyc—Cyc—Phe—Phe—X—R²    IIc

R¹—Cyc—Cyc—Cyc—Phe—X—R²    IId

R¹—Cyc—Cyc—Cyc—Cyc—X—R²    IIe

R¹—Cyc—Phe—Phe—Cyc—X—R²    IIf

In the compounds of the formulae above and below, X is preferably Q—CF$_2$—, in which Q is —O—, —S— or —CO—.

In the compounds of the formula I which contain a terminal —X—R² group, R² is H, halogen or CN.

In the compounds of the formula F having a terminal —Q—CF$_2$—R² group in which Q is O, R² is chlorine or CN, and in those in which Q is S, R² is fluorine, chlorine or CN.

The terminal group X—R² is thus preferably
—CO—CF$_3$
—CO—CF$_2$—H
—CO—CF$_2$—CN
—CO—CF$_2$—Cl
—S—CF$_3$
—S—CF$_2$—Cl
—S—CF$_2$—CN
—O—CF$_2$—Cl
—O—CF$_2$—CN R¹ is preferably alkyl, furthermore alkoxy. R² is preferably alkyl, alkoxy, F, Cl or CN. A¹, A², A² and/or A⁴ are preferably Phe, Cyc, Che, Pyr or Dio. The compounds of the formula I preferably contain not more than one of the radicals Bi, Pyd, Pyr, Dio or Dit.

Preferred compounds of the formula I and of all the sub-formulae are those in which A¹, A², A³ and/or A⁴ are 1,4-phenylene which is monosubstituted or disubstituted by F or monosubstituted by CN. These are, in particular, 2-fluoro-1,4-phenylene, 3-fluoro-1,4-phenylene and 2,3-difluoro-1,4-phenylene, and 2-cyano-1,4-phenylene and 3-cyano-1,4-phenylene.

Z¹ and Z² are preferably a single bond, —CO—O—, —O—CO— and —CH$_2$CH$_2$—, and secondarily preferably —CH$_2$O— and —OCH$_2$—.

If one of the radicals R¹ and R² is halogen, it is preferably F, Cl, Br or I.

If R¹ and/or R² are an alkyl radical and/or an alkoxy radical, it may be straight-chain or branched. It is preferably straight-chain, has 2, 3, 4, 5, 6 or 7 C atoms and is accordingly preferably ethyl, propyl, butyl, pentyl, hexyl, heptyl, ethoxy, propoxy, butoxy, pentoxy, hexoxy or heptoxy, furthermore methyl, octyl, nonyl, decyl, undecyl, dodecyl, tridecyl, tetradecyl, pentadecyl, methoxy, octoxy, nonoxy, decoxy, undecoxy, dodecoxy, tridecoxy or tetradecoxy.

Oxaalkyl is preferably straight-chain 2-oxapropyl (=methoxymethyl), 2- (=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If R¹ and/or R² are an alkenyl radical, it may be straight-chain or branched. It is preferably straight-chain and has 2 to 10 C atoms. It is accordingly particularly vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6-or -7-enyl, non-1-, -2-, -3-, -4-, -5-, -6-, -7- or -8-enyl, or dec-1-, -2-, -3-, -4-, -5-, -6-, -7-, -8- or -9-enyl.

If R¹ and/or R² are an alkyl radical in which one CH$_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 C atoms. They are accordingly particularly acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl and 4-(methoxycarbonyl)butyl.

If R¹ and/or R² are an alkenyl radical in which one CH$_2$ group has been replaced by CO or CO—O or O—CO, it may be straight-chain or branched. It is preferably straight-chain and has 4 to 13 C atoms. It is accordingly particularly acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

Compounds of the formula I which contain wing groups R¹ and/or R² which are suitable for polymerization reactions are suitable for the preparation of liquid-crystalline polymers.

Compounds of the formula I containing branched wing groups R¹ and/or R² may occasionally be of importance due to better solubility in the customary liquid-crystalline base materials, but in particular as chiral dopants if they are optically active. Smectic compounds of this type are suitable as components of ferroelectric materials.

Compounds of the formula I having S$_A$ phases are suitable, for example, for thermally addressed displays.

Branched groups of this type generally contain not more than one chain branch. Preferred branched radicals R¹ and/or R² are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy, 1-methylheptoxy, 2-oxa-3-methylbutyl, 3-oxa-4-methylpentyl, 4-methylhexyl, 2-nonyl, 2-decyl, 2-dodecyl, 6-methyloctoxy, 6-methyloctaroyloxy, 5-methylheptyloxycarbonyl, 2-methylbutyryloxy, 3-methylvaleryloxy, 4-methylhexanoyloxy, 2-chloropropionyloxy, 2-chloro-3-methylbutyryloxy, 2-chloro-4-methylvaleryloxy, 2-chloro-3-methylvaleryloxy, 2-methyl-3-oxapentyl and 2-methyl-3-oxahexyl.

If $R^1$ or $R^2$ is an alkyl radical in which two or more $CH_2$ groups have been replaced by —O— and/or —CO—O—, it may be straight-chain or branched. It is preferably branched and has 3 to 12 C atoms. It is accordingly particularly biscarboxymethyl, 2,2-biscarboxyethyl, 3,3-biscarboxypropyl, 4,4-biscarboxybutyl, 5,5-biscarboxypentyl, 6,6-biscarboxyhexyl, 7,7-biscarboxyheptyl, 8,8-biscarboxyoctyl, 9,9-biscarboxynonyl, 10,10-biscarboxydecyl, bis(methoxycarbonyl)methyl, 2,2-bis(methoxycarbonyl)ethyl, 3,3-bis(methoxycarbonyl)propyl, 4,4-bis(methoxycarbonyl)butyl, 5,5-bis(methoxycarbonyl)pentyl, 6,6-bis(methoxycarbonyl)hexyl, 7,7-bis(methoxycarbonyl)heptyl, 8,8-bis(methoxycarbonyl)octyl, bis(ethoxycarbonyl)methyl, 2,2-bis(ethoxycarbonyl)ethyl, 3,3-bis(ethoxycarbonyl)propyl, 4,4-bis(ethoxycarbonyl)butyl or 5,5-bis(ethoxycarbonyl)hexyl.

Compounds of the formula I which contain wing groups $R^1$ and/or $R^2$ which are suitable for polycondensations are suitable for the preparation of liquid-crystalline polycondensates.

The formula I covers the racemates of these compounds and the optical antipodes, and mixtures thereof.

Of these compounds of the formula I and the sub-formulae, those are preferred in which at least one of the radicals present therein has one of the preferred meanings indicated.

In the compounds of the formula I, those stereoisomers in which the rings Cyc and piperidine are trans-1,4-disubstituted are preferred. Those of the abovementioned formulae which contain one or more groups Pyd, Pyr and/or Dio in each case include the two 2,5-positional isomers.

Particularly preferred compounds of the sub-formula I1 are those of the sub-formulae I1a to I1m:

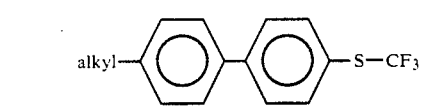

I1a

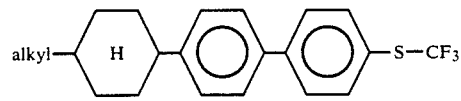

I1b

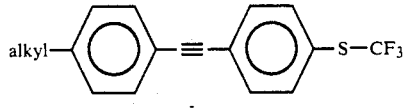

I1c

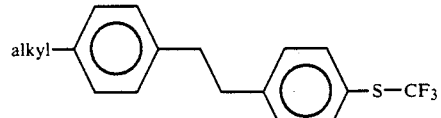

I1d

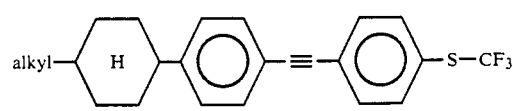

I1e

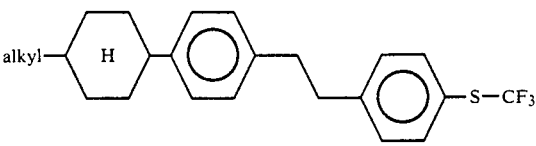

I1f

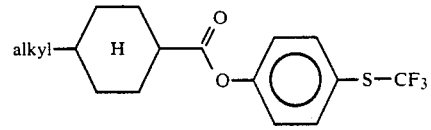

I1g

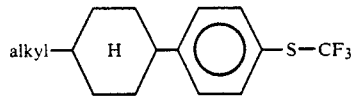

I1h

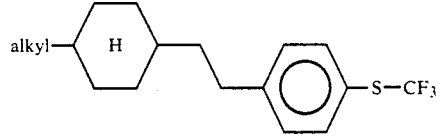

I1i

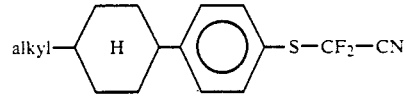

I1j

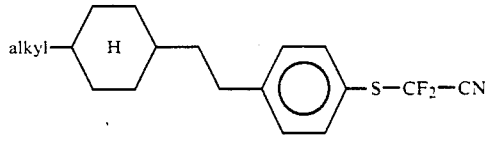

I1k

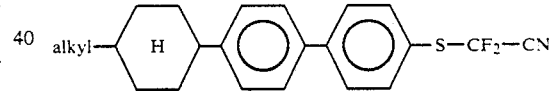

I1l

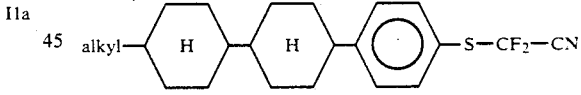

I1m

Particularly preferred compounds of the sub-formulae I2 are those of the sub-formulae I2a to I2c:

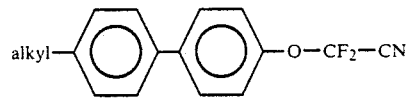

I2a

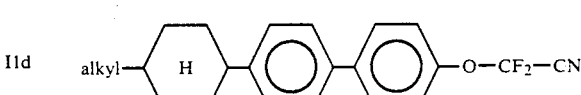

I2b

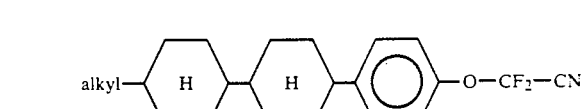

I2c

Particularly preferred compounds of the sub-formula I3 are those of the sub-formulae I3a to I3g:

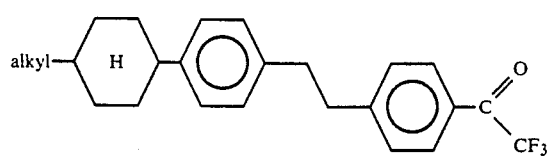  I3a
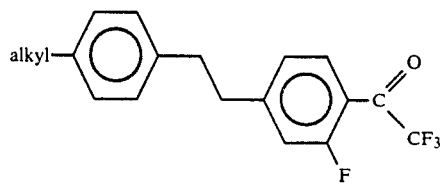  I3b
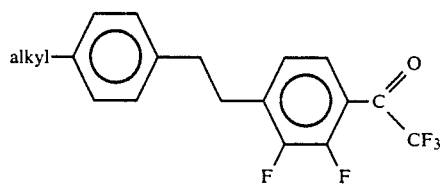  I3c
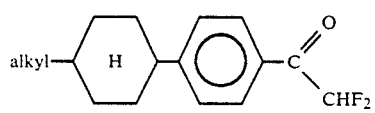  I3d
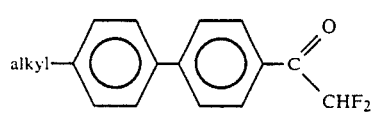  I3e
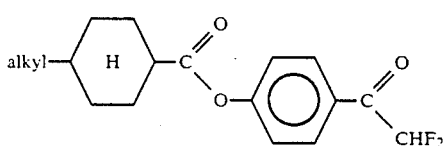  I3f
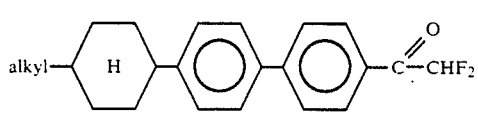  I4g
Of the compounds of the formula I4 in which the group X connects two cyclic groups A² and A³ or A⁴ to one another
$$R^1-(A^1-Z^1)_m-A^2-X-(A^3-Z^2)_n-A^4-R^2 \quad I4$$
in which A⁴ is not a single bond, those of the sub-formulae I4a to I4t are particularly preferred:
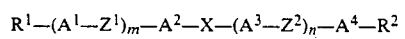  I4a
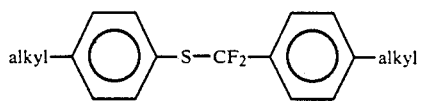  I4b
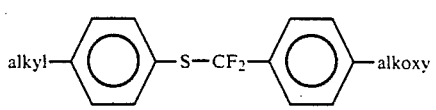  I4c
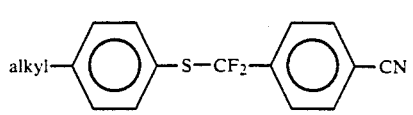  I4d... 
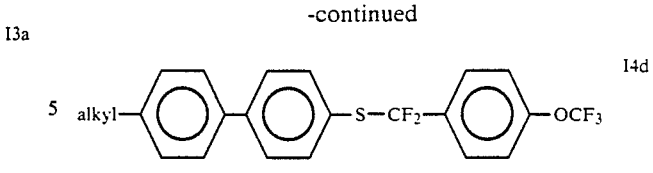  I4d
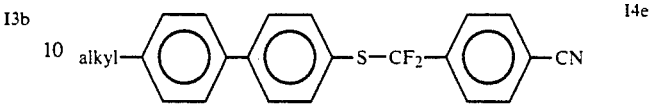  I4e
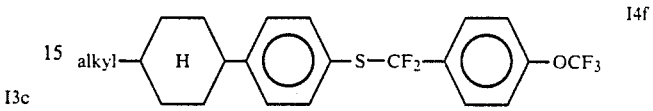  I4f
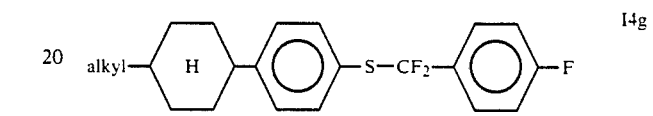  I4g
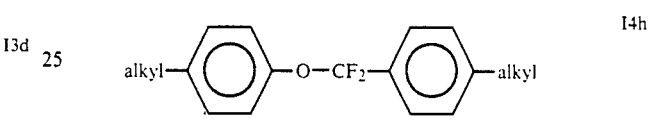  I4h
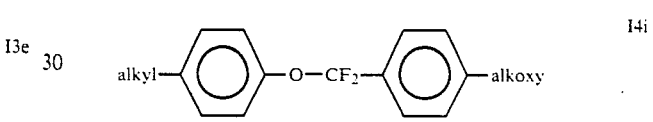  I4i
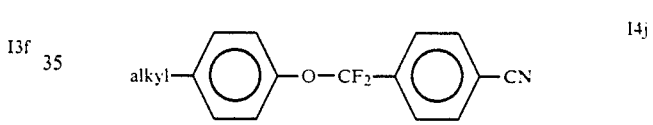  I4j
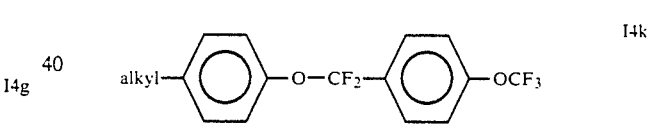  I4k
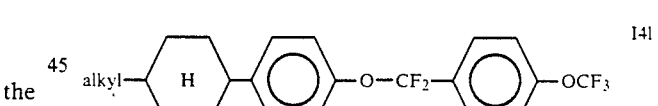  I4l
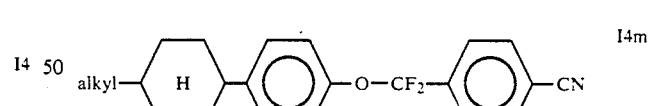  I4m
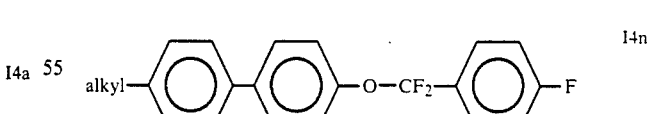  I4n
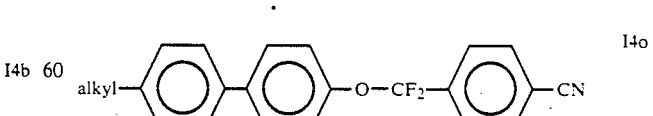  I4o
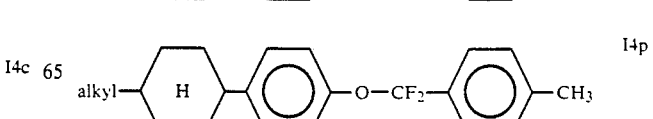  I4p

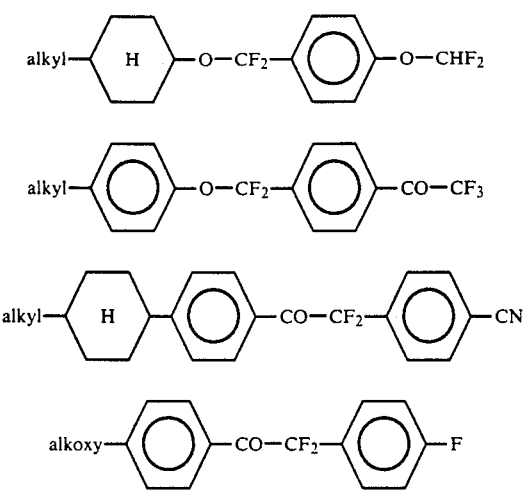

In the above compounds of the sub-formulae I1a to I1g, I2a to I2c, I3a to I3f and I4a to I4t, alkyl- and alkoxy- are in each case alkyl or alkoxy groups having 1 to 12 C atoms.

The 1,4-cyclohexenylene group preferably has the following structures:

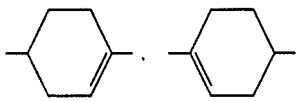

The compounds of the formula I are prepared by methods known per se, as described in the literature (for example in the standard works, such as Houben-Weyl, Methoden der Organischen Chemie [Methods of Organic Chemistry], Georg-Thieme-Verlag, Stuttgart, Vol. IX, pp. 867 ff.), to be precise under reaction conditions which are known and suitable for the reactions mentioned. Use can also be made here of variants which are known per se, but are not described in great detail here.

The aryl trifluorothiomethyl ethers according to the invention can be prepared, for example, by reacting thioaryl compounds with trifluoroiodomethane under reaction conditions which are suitable for the Reimer-Tiemann reaction between phenols and chloroform [for example V. N. Boiko, G. M. Shchupak, L. M. Yagupolskij, Zh. Org. Khim. 13 (1977), 1057].

Difluoroaryl ethers and aryl difluorothioethers according to the invention can also be prepared, for example, by reacting, for example, appropriate nitrobenzenes or fluorobenzenes which additionally carry at least one electron-withdrawing substituent directly with alkali metal difluoroalkoxy compounds or with alkali metal difluorothioalkyl compounds, F or NO2 being substituted by the difluoroalkoxy or difluorothioalkyl radical [J. P. Idoux et al., J. Org. Chem. 50, 1976 (1985)].

Difluoroalkyl compounds of the formula I can be prepared, for example, by reacting aldehydes or ketones with dialkylaminosulfur trifluoride, for example DAST (diethylaminosulfur trifluoride) [W. J. Middleton, J. Org. Chem. 40, 574 (1975)] or sulfur tetrafluoride [A. Haas, M. Spitzer, M. Lieb, Chem. Ber. 121 (1988), 1329].

Trifluoroacetylaryl and difluoroacetylaryl compounds of the formula I (Q=CO) can be prepared, for example, by reacting the appropriate aryl compounds with trifluoroacetyl chloride or difluoroacetyl chloride with one another under Friedel-Crafts conditions [for example J. H. Simons, E. O. Ramler, J. Am. Chem. Soc. 65 (1943), 389].

The cyanodifluoromethoxy and cyanodifluoromethylthio compounds of the formula I can be prepared, for example, by reacting the corresponding alcoholates or thioalcoholates with chlorodifluoroacetic acid and converting the carboxyl group in the carboxydifluoromethoxy or carboxydifluoromethylthio compounds obtained in this way into a cyano group in a manner known per se [for example L. M. Yagupolskii, V. A. Korinko, Zh. Obshch. 37 (197), 1717].

If desired, the starting materials can also be formed in situ by not isolating them from the reaction mixture, but instead reacting them further to form the compounds of the formula I.

Thus, the compounds of the formula I can be prepared by reducing a compound which contains one or more reducible groups and/or C—C bonds in place of H atoms, but otherwise corresponds to the formula I.

Suitable reducible groups are preferably carbonyl groups, in particular keto groups, furthermore for example, free or esterified hydroxyl groups or aromatically bound halogen atoms. Preferred starting materials for the reduction correspond to the formula I, but can contain a cyclohexene ring or cyclohexanone ring in place of a cyclohexane ring and/or can contain a —CH=CH— group in place of a —CH2CH2— group and/or can contain a —CO— group in place of a —CH2— group and/or can contain a free or functionally (for example in the form of its p-toluenesulfonate) derived OH group in place of an H atom.

The reduction can be carried out, for example, by catalytic hydrogenation at temperatures between about 0° and about 200° and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are preferably noble metals, such as Pt or Pd, which can be employed in the form of oxides (for example PtO2 or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, preferably in aqueous-alcoholic solution or in the heterogeneous phase with water/toluene at temperatures between about 80° and 120°) or Wolff-Kishner (using hydrazine, preferably in the presence of alkali, such as KOH or NaOH, in a high-boiling solvent, such as diethylene glycol or triethylene glycol, at temperatures between about 100° and 200°) to form the corresponding compounds of the formula I which contain alkyl groups and/or —CH2CH2— bridges.

In addition, reductions using complex hydrides are possible. For example, arylsulfonyloxy groups can be removed reductively using LiAlH4, in particular p-toluenesulfonyloxymethyl groups are reduced to methyl groups, preferably in an inert solvent, such as diethyl ether or THF, at temperatures of between about 0° and 100°. Double bonds can be hydrogenated using NaBH4 or tributyltin hydride in methanol.

Compounds of the formula I which contain 1,4-cyclohexenylene radicals in place of 1,4-phenylene radicals but otherwise correspond to the formula I can be oxidized, for example, using DDQ (dichlorodicyanobenzoquinone) in a suitable solvent.

Esters of the formula I can also be obtained by esterification of appropriate carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

Suitable reactive derivatives of the carboxylic acids mentioned are, in particular, the acyl halides, above all the chlorides and bromides, furthermore the anhydrides, for example also mixed anhydrides, azides or esters, in particular alkyl esters having 1–4 C atoms in the alkyl group.

Suitable reactive derivatives of the alcohols or phenols mentioned are, in particular, the corresponding metal alkoxides or phenoxides, preferably of an alkali metal such as sodium or potassium.

The esterification is advantageously carried out in the presence of an inert solvent. Highly suitable solvents are, in particular, ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane, dichloromethane or tetrachloroethylene, and sulfoxides, such as dimethyl sulfoxide or sulfolane.

In order to prepare nitriles of the formula I, appropriate acid amides, for example those in which a $CONH_2$ group replaces the CN radical, are dehydrated. The amides can be obtained, for example, from appropriate esters or acyl halides by reaction with ammonia. Suitable water-eliminating agents are, for example, inorganic acid chlorides, such as $SOCl_2$, $PCl_3$, $PCl_5$, $POCl_3$, $SO_2Cl_2$, $COCl_2$, furthermore $P_2O_5$, $P_2S_5$, $AlCl_3$ (for example as a double compound with NaCl), aromatic sulfonic acids and sulfonyl halides. The reaction can be carried out in the presence or absence of an inert solvent at temperatures between about 0° and 150°; suitable solvents are, for example, bases, such as pyridine or triethylamine, aromatic hydrocarbons, such as benzene, toluene or xylene, or amides, such as DMF.

To prepare the abovementioned nitriles of the formula I, it is also possible to react appropriate acyl halides, preferably the chlorides, with sulfamide, preferably in an inert solvent, such as tetramethylene sulfone, at temperatures between about 80° and 150°, preferably at 120°. After customary work-up, the nitriles can be isolated directly.

Ethers of the formula I can be obtained by etherification of corresponding hydroxyl compounds, preferably corresponding phenols, the hydroxyl compound expediently first being converted into a corresponding metal derivative, for example into the corresponding alkali metal alcoholate or alkali metal phenolate by treatment with NaH, $NaNH_2$, NaOH, KOH, $Na_2CO_3$ or $K_2CO_3$. This can then be reacted with the appropriate alkyl halide, sulfonate or dialkyl sulfate, expediently in an inert solvent, such as acetone, 1,2-dimethoxyethane, DMF or dimethyl sulfoxide, or also an excess of aqueous or aqueous-alcoholic NaOH or KOH, at temperatures between about 20° and 100°.

To prepare nitriles of the formula I, it is also possible to react appropriate chlorine, bromine or iodine compounds of the formula I with a cyanide, preferably with a metal cyanide, such as NaCN, KCN or $Cu_2(CN)_2$, for example in the presence of pyridine in an inert solvent, such as DMF or N-methylpyrrolidone, at temperatures between 20° and 200°.

Compounds of the formula I in which $A^1$ is substituted by at least one F atom and/or one CN group can also be obtained from the corresponding diazonium salts by replacement of the diazonium group by a fluorine atom or by a CN group, for example by the methods of Schiemann or Sandmeyer.

Dioxane derivatives and dithiane derivatives of the formula I are expediently prepared by reacting an appropriate aldehyde (or a reactive derivative thereof) with an appropriate 1,3-diol (or a reactive derivative thereof) or an appropriate 1,3-dithiol, preferably in the presence of an inert solvent, such as benzene or toluene, and/or in the presence of a catalyst, for example a strong acid such as sulfuric acid, benzenesulfonic acid or p-toluenesulfonic acid, at temperatures between about 20° and about 150°, preferably between 80° and 120°. Suitable reactive derivatives of the starting materials are primarily acetals.

Some of the aldehydes, 1,3-diols and 1,3-dithiols mentioned, and some of the reactive derivatives thereof, are known, but they can all be prepared without difficulties from compounds known from the literature by standard methods of organic chemistry. For example, the aldehydes can be obtained by oxidation of corresponding alcohols or by reduction of nitriles or corresponding carboxylic acids or derivatives thereof, the diols can be obtained by reduction of corresponding diesters, and the dithiols can be obtained by reaction of nitriles or corresponding dihalides with NaSH.

The liquid-crystalline media according to the invention preferably contain 2 to 40, in particular 4 to 30, components as further components besides one or more compounds according to the invention. These media very particularly preferably contain 7 to 25 components besides one or more compounds according to the invention. These further components are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl esters of cyclohexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

The most important compounds suitable as further components of media according to the invention can be characterized by the formulae 1, 2, 3, 4 and 5:

$$R'-L-E-R'' \quad 1$$

$$R'-L-COO-E-R'' \quad 2$$

$$R'-L-OOC-E-R'' \quad 3$$

$$R'-L-CH_2CH_2-E-R'' \quad 4$$

$$R'-L-C\equiv C-E-R'' \quad 5$$

In the formulae 1, 2, 3, 4 and 5, L and E, which may be identical or different, are in each case, independently of one another, a bivalent radical from the group formed by —Phe—, —Cyc—, —Phe—Phe, —Phe—Cyc—, —Cyc—Cyc—, —Pyr—, —Dio—, —G—Phe— and —G—Cyc— and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably contain one or more components selected from the compounds of the formulae 1, 2, 3, 4 and 5 in which L and E are selected from the group comprising Cyc, Phe and Pyr and simultaneously one or more components selected from the compounds of the formulae 1, 2, 3, 4 and 5 in which one of the radicals L and E is selected from the group comprising Cyc, Phe and Pyr and the other radical is selected from the group comprising —Phe—Phe—, —Phe—Cyc—, —Cyc—Cyc—, —G—Phe— and —G—Cyc—, and optionally one or more components selected from the compounds of the formulae 1, 2, 3, 4 and 5 in which the radicals L and E are selected from the group comprising —Phe—Cyc—, —Cyc—Cyc—, —G—Phe— and —G—Cyc—.

In the compounds of the sub-formulae 1a, 2a, 3a, 4a and 5a, R' and R" are in each case, independently of one another, alkyl, alkenyl, alkoxy, alkenyloxy or alkanoyloxy having up to 8 carbon atoms. In most of these compounds, R' and R" are different from one another, one of these radicals usually being alkyl or alkenyl. In the compounds of the sub-formulae 1b, 2b, 3b, 4b and 5b, R" is —CN, —CF$_3$, —OCF$_3$, OCF$_2$H, F, Cl or —NCS; in this case, R has the meaning given for the compounds of the sub-formulae 1a to 5a and is preferably alkyl or alkenyl. However, other variants of the proposed substituents in the compounds of the formulae 1, 2, 3, 4 and 5 are common. Many such substances or alternatively mixtures thereof are commercially available. All these substances can be obtained by methods which are known from the literature or analogously thereto.

Besides components from the group comprising the compounds 1a, 2a, 3a, 4a and 5a (Group 1), the media according to the invention also contain components from the group comprising the compounds 1b, 2b, 3b, 4b and 5b (Group 2), whose proportions are preferably as follows:

Group 1: 20 to 90%, in particular 30 to 90%,
Group 2: 10 to 80%, in particular 10 to 50%, the sum of the proportions of the compounds according to the invention and of the compounds from Groups 1 and 2 adding up to 100%.

The media according to the invention preferably contain 1 to 40%, in particular preferably 5 to 30%, of compounds according to the invention. Further preferred media are those which contain more than 40%, in particular 45 to 90%, of compounds according to the invention. The media preferably contain three, four or five compounds according to the invention.

The media according to the invention are prepared in a manner which is customary per se. In general, the components are dissolved in one another, expediently at elevated temperature. By means of suitable additives, the liquid-crystalline phases can be modified in accordance with the invention in a manner such that they can be used in all types of liquid-crystal display elements which have hitherto been disclosed. Additives of this type are known to those skilled in the art and are described in detail in the literature (H. Kelker/R. Hatz, Handbook of Liquid Crystals, Verlag Chemie, Weinheim, 1980). For example, pleochroic dyes can be added for the production of coloured guest-host systems, or substances can be added to modify the dielectric anisotropy, the viscosity and/or the orientation of the nematic phases.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, if any, cited above and below, and of corresponding application Federal Republic of Germany P 39 08 945.2, filed Mar. 18, 1989, are hereby incorporated by reference.

mp.=melting point, cp.=clear point. "Customary work-up" means that water is added, the mixture is extracted with methylene chloride, the organic phase is separated off, dried and evaporated, the product is purified by crystallization and/or chromatography.

In addition, the abbreviations have the following meanings: C: crystalline-solid state, S: smectic phase (the index characterizes the phase type), N: nematic state, Ch: cholesteric phase, I: isotropic phase. The number between two symbols indicates the conversion temperature in degrees Celsius.

DAST—Diethylaminosulfur trifluoride
DCC—Dicyclohexylcarbodiimide
DDQ—Dichlorodicyanobenzoquinone
DIBALH—Diisobutylaluminium hydride
KOT—Potassium tertiary-butanolate
THF—Tetrahydrofuran
pTSOH—p-Toluenesulfonic acid

EXAMPLE 1

4-(4-trans-Pentylcyclohexyl)-4'-(trifluoromethylthio)-biphenyl

First 100 ml of liquid ammonia, then 0.125 mol of trifluoroiodomethane are condensed into a three-neck flask containing 0.1 mol of 4-(trans-4-pentylcyclohexyl)-4'-mercaptobiphenyl (prepared by reduction using zinc and hydrochloric acid from the corresponding sulfonyl chloride, obtained from the hydrocarbon by treatment with chlorosulfonic acid) with cooling to −60° to −70°. The mixture is irradiated for 2 hours using a mercury vapour lamp. The ammonia is subsequently allowed to evaporate; the residue is treated with 50 ml of 5% sodium hydroxide solution and the mixture is extracted with ether (3×100 ml); the combined ether phases are washed with water, then with 5% strength sodium sulfite solution and again with water. The ether is removed by distillation and the residue is recrystallized twice from ethanol.

The product is obtained as a solid having C 79 N 106 I.

The following are prepared analogously:

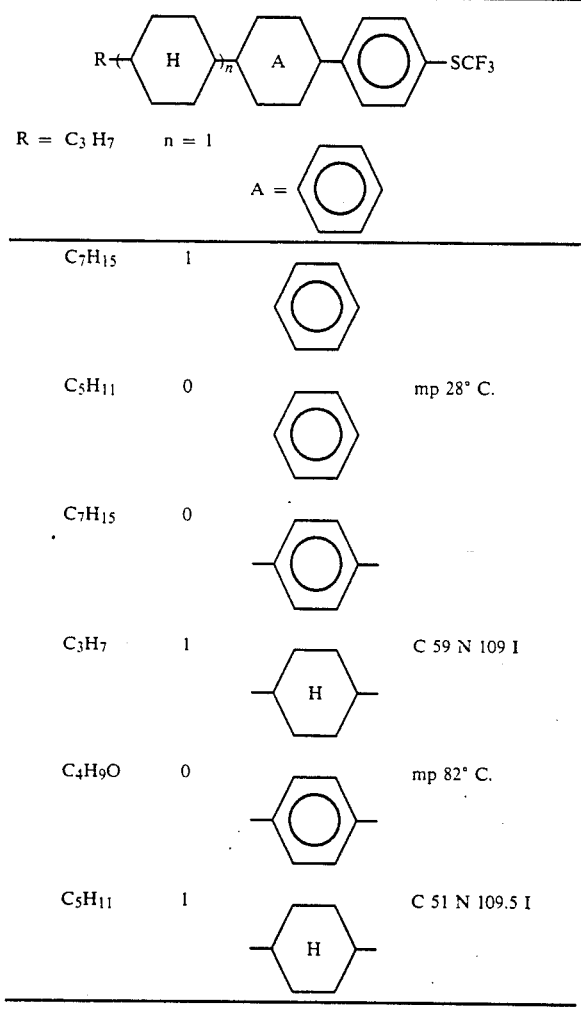

EXAMPLE 2

Difluoro(4-pentylphenyl) (4-pentylphenylthio)methane 1 mol of 4-pentylbenzaldehyde are reacted with 2 mol of sulfur tetrafluoride for 18 hours at 100° C. in a nickel autoclave after 3 drops of water have been added. When the reaction is complete, the gaseous reaction products are eliminated by passing them through ice-cool sodium hydroxide solution. The residue in the autoclave is taken up in 500 ml of dichloromethane, and the solution is neutralized by shaking with dilute sodium hydroxide solution. The aqueous phase is extracted with dichloromethane (2×100 ml), the organic phases are combined, the solvent is removed by distillation, and the residue is distilled at 80°-90° in a water-pump vacuum. The distillate is dissolved in 500 ml of tetrachloromethane with 50 ml of bromine, and the solution is irradiated under reflux for 3 days using a mercury vapour lamp. After cooling, the mixture is washed with sodium sulfite solution and with water, the solvent is subsequently removed by distillation, and the residue is distilled at 0.1 mm Hg and 80° C.

The distillate obtained is added to a solution of the sodium salt of 4-pentylthiophenol (prepared from 0.6 mol of thiophenol and 0.6 mol of sodium) in 500 ml of dimethylformamide. The mixture is stirred at 50° for 16 hours, 500 ml of ether are then added, and the mixture is washed by shaking with water (3×500 ml). After the ether has been removed by distillation, the residue is transferred to a short silica gel column and eluted with petroleum ether. After the petroleum ether has been removed by distillation, the product is recrystallized twice from ethanol.

The following are prepared analogously:

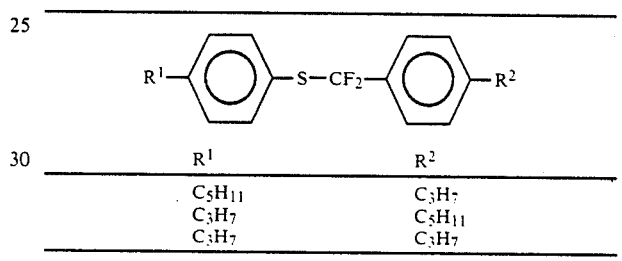

EXAMPLE 3

Difluoro(4-heptylphenyloxy) (4-pentylphenyl)methane

The preparation is carried out analogously to Example 2 using a solution of 0.6 mol of sodium 4-heptylphenolate (prepared from phenol and sodium hydride) in 600 ml of DMF. The reaction mixture is kept at 80° for 24 hours.

The following are prepared analogously:

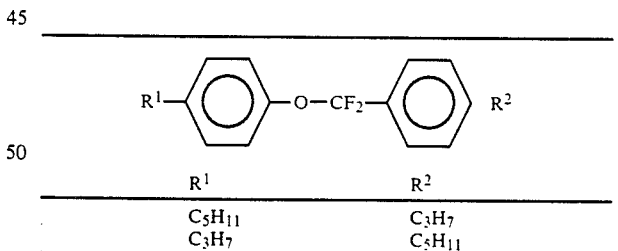

EXAMPLE 4

4-(trans-4-Pentylcyclohexyl)-4'-trifluoroacetylbiphenyl 0.5 mol of 4-(trans-4-pentylcyclohexyl)biphenyl, 500 ml of carbon sulfide and 0.5 mol of aluminium chloride are introduced into a three-neck flask fitted with a dry-ice reflux condenser. After the mixture has been cooled to −30°, 0.5 mol of trifluoroacetyl chloride are condensed in. The mixture is then allowed to warm to 0° and stirred at this temperature for 6 hours then at room temperature for 14 hours. The reaction mixture is poured onto a mixture of ice and dilute hydrochloric acid. The organic phase is separated off, and the aqueous phase is extracted by shaking with dichloromethane (2×50 ml). The organic phases are combined, the solvents removed by distillation and the product is recrystallized twice from ethanol.

The following are prepared analogously:

R¹—A—(⌬)ₙ—⌬—CO—CF₃

| R¹ | n | A |
|---|---|---|
| C₃H₇ | 1 | A |
| C₇H₁₅ | 1 | H |
| C₅H₁₁ | 0 | H | mp 13° C. |
| C₇H₁₅ | 0 | ⌬ | C 19 N (−5.1) I |

(Note: A column shows ring types: A, H, H, ⌬(phenyl), H)

| R¹ | n | A | |
|---|---|---|---|
| C₃H₇ | 1 | A | |
| C₇H₁₅ | 1 | H | |
| C₅H₁₁ | 0 | H | mp 13° C. |
| C₇H₁₅ | 0 | phenyl | C 19 N (−5.1) I |

Using 2-difluoro-2-chloroacetyl chloride as the starting compound, the following are obtained analogously:

R¹—A—(⌬)ₙ—⌬—CO—CF₂—Cl

| R¹ | n | A | |
|---|---|---|---|
| C₃H₇ | 0 | A | |
| C₅H₁₁ | 0 | H | |
| C₇H₁₅ | 1 | H | C 52 N 124 I |

EXAMPLE 5

4-Difluoroacetyl-4'-(trans-4-propylcyclohexyl)biphenyl

The preparation is carried out analogously to Example 4 from 0.5 mol of 4-(trans-4-propylcyclohexyl)biphenyl and 0.5 mol of difluoroacetyl chloride.

The following are prepared analogously:

R¹—H—(⌬)ₙ—⌬—COCHF₂

| R¹ | n | |
|---|---|---|
| C₅H₁₁ | 1 | |
| C₇H₁₅ | — | |
| C₅H₁₁ | 0 | mp 39° C. |

EXAMPLE 6

2-(4-Cyanophenyl)-2,2-difluoro-1-[4-(trans-4-pentylcyclohexyl)phenyl]ethanone 0.08 mol of bromodifluoro(4-cyanophenyl)methane [prepared by the method of A. Haas, M. Spitzer, M. Lieb, Chem. Ber. 121 (1988)] are dissolved in 50 ml of THF; at −78°, 50 ml of a 1.6 molar solution of butyllithium in hexane are added dropwise. The mixture is stirred for 15 minutes, and then a solution of 0.08 mol of 4-(trans-4-pentylcyclohexyl)benzonitrile in 60 ml of THF is added dropwise. The mixture is allowed to warm to 0° and then poured into a mixture of ice and dilute hydrochloric acid. The organic phase is separated off, and the aqueous phase is extracted with ether (50 ml) and dichloromethane (2×25 ml). The organic phases are combined, the solvents are removed by distillation, and the residue is chromatographed on a silica gel column using petroleum ether/ether as the eluent. After the eluate has been evaporated, the residue is recrystallized from ethanol.

The following are prepared analogously:

R¹—H—(⌬)ₙ—⌬—CO—CF₂—⌬—R²

| R¹ | n | R² |
|---|---|---|
| C₃H₇ | 1 | CN |
| C₇H₁₅ | 1 | CN |
| F₃CO | 0 | C₅H₁₁ |
| F | 0 | C₅H₁₁ |

EXAMPLE 7

4-(Cyanodifluoromethoxy)-4'-(trans-4-propylcyclohexyl)biphenyl 0.11 mol of sodium hydride is added in portions to a solution of 0.10 mol of 4-(trans-4-propylcyclohexyl)biphenyl-4'-ol and 0.1 mol of chlorodifluoroacetic acid in 100 ml of DMF. The mixture is subsequently warmed at 80° for 16 hours. 250 ml of isopropanol are then added, and the mixture is evaporated on a rotary evaporator. The addition of isopropanol and the evaporation are repeated twice, so that the residue only contains traces of DMF. Phosphorus pentachloride (0.1 mol) is then added in one portion. The mixture warms and is kept at 60° for 3 hours by means of external heating. After filtration through a glass frit, the product is recrystallized from petroleum ether/carbon disulfide (with cooling to −70°).

The acid chloride obtained in this way is taken up in 50 ml of dioxane and treated with 10 ml of 32% strength aqueous ammonia solution. After the reaction has subsided, the mixture is stirred for a further 1 hour, 50 ml of water are added, and the mixture is stirred for a further hour; the precipitated product is subsequently filtered off with suction, washed with water and dried in vacuo; it is then heated at about 100° C. for 3 hours with 0.07 mol of phosphorus pentoxide. After cooling, the residue is extracted with toluene in a Soxhlet extractor. The extracts are evaporated in vacuo, and the residue obtained is recrystallized twice from ethanol.

The following are prepared analogously:

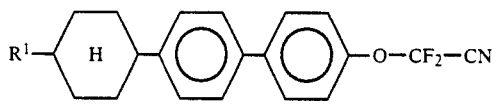

| $R^1$ |
| --- |
| $C_5H_{11}$ |
| $C_7H_{15}$ |

EXAMPLE 8

Cyanodifluoromethyl 4-(trans-4-pentylcyclohexyl)phenyl thioether

The preparation is carried out analogously to Example 7, starting from 0.1 mol of 4-(trans-4-pentylcyclohexyl)thiophenol (prepared by zinc/glacial acetic acid reduction of the corresponding sulfonyl chloride, obtained from the parent hydrocarbon using chlorosulfonic acid).

The following are prepared analogously:

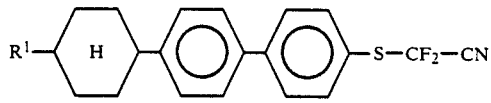

| $R^1$ |
| --- |
| $C_3H_7$ |
| $C_7H_{15}$ |

EXAMPLE 9

0.1 mol of phenol and 0.1 mol of trifluoroacetyl chloride are reacted analogously to Example 4 to give 4-trifluoroacetylphenol. The latter is esterified using carboxylic acids and DCC. With p-pentylbenzoic acid, 4-trifluoroacetylphenyl pentylbenzoate, mp. 27° C., $\Delta\epsilon = 26.7$, is obtained.

The following are prepared analogously:

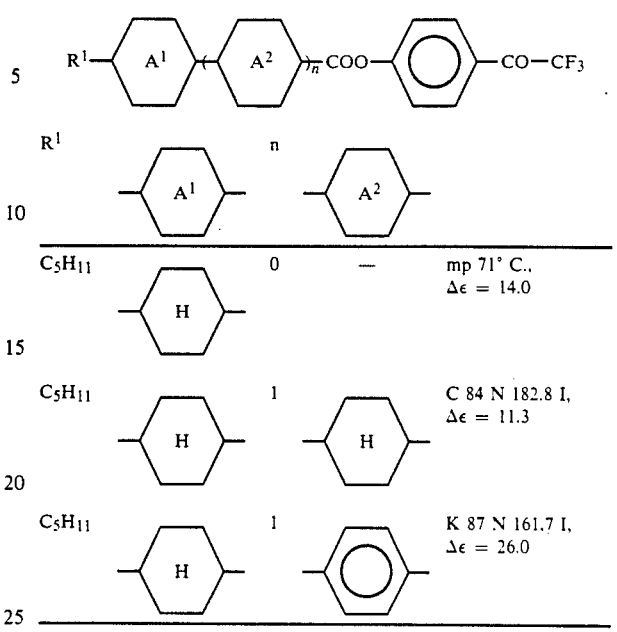

| $R^1$ | n | | |
| --- | --- | --- | --- |
| $C_5H_{11}$ (H) | 0 | — | mp 71° C., $\Delta\epsilon = 14.0$ |
| $C_5H_{11}$ (H) | 1 | (H) | C 84 N 182.8 I, $\Delta\epsilon = 11.3$ |
| $C_5H_{11}$ (H) | 1 | (phenyl) | K 87 N 161.7 I, $\Delta\epsilon = 26.0$ |

EXAMPLE 10

A mixture of 0.1 mol of trifluoroacetylphenol, 0.11 mol of trans-4-pentylcyclohexylmethyl bromide, 0.3 mol of $K_2CO_3$ and 250 ml DMF is heated at 140° C. for 10 hours. Customary work-up and crystallization give 4-(trans-4-pentylcyclohexylmethoxy)-1-trifluoroacetylbenzene, mp. 60° C., $\Delta\epsilon = 13.7$.

MIXTURE EXAMPLE A

A liquid-crystalline medium is prepared, comprising the following components:
11% by weight of trans-1-p-propylphenyl-4-pentylcyclohexane
16% by weight of 4′-(2-(trans-4-propylcyclohexyl)ethyl)-4-ethyl-2-fluorobiphenyl
10% by weight of 4′-(2-(trans-4-propylcyclohexyl)ethyl)-4-pentyl-2-fluorobiphenyl
9% by weight of 4-ethyl-4′-(trans-4-propylcyclohexyl)-biphenyl
4% by weight of 4,4′-bis(trans-4-propylcyclohexyl)-biphenyl
4% by weight of 4,4′-bis(trans-4-pentylcyclohexyl)-biphenyl
4% by weight of 4-(trans-4-propylcyclohexyl)-4′-(trans-4-pentylcyclohexyl)-biphenyl
6% by weight of 4,4′-bis(trans-4-propylcyclohexyl)-2-fluorobiphenyl
6% by weight of 4,4′-bis(trans-4-pentylcyclohexyl)-2-fluorobiphenyl
30% by weight of 4′-(trans-4-pentylcyclohexyl)-4-(trifluoromethylthio)biphenyl.

This medium has a nematic phase range of above 90° C., a threshold voltage of about 4 V and an unusually high resistance in the display and is thus particularly suitable for use in active matrix displays.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

Alkyl or alkenyl of the substituents $R^1$ and $R^2$ being mono- or polysubstituted by halogen denotes a mono-, di- or perhalogenated, in particular a mono-, di-, or perfluorinated, alkyl or alkenyl groups. In the case that one or two $CH_2$ groups of the substituents $R^1$ and $R^2$ are replaced by

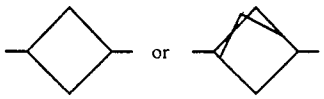

the resulting radical exhibits 5 to 20 C atoms.

What is claimed is:

1. A difluoromethylene compound of the formula I $$R^1-(A^1-Z^1)_m-A^2-S-CF_2-R^2$$

in which
R$^1$ is alkyl or alkenyl of up to 15 C atoms, in each case optionally unsubstituted, monosubstituted by CN or CF$_3$, or mono- or poly-substituted by halogen, or optionally having one or two CH$_2$ groups, in each case independently of one another, replaced by —O—,

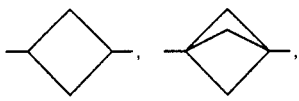

—CO—, —CO—O—, —O—CO— or —O—CO—O— in a manner such that O atoms are not linked directly to one another,
R$^2$ is F, Cl or —CN,
A$^1$ and A$^2$ independently of one another, are
(a) trans-1,4-cyclohexylene in which, optionally one or two non-adjacent CH$_2$ groups may be replaced by —O— and/or —S—,
(b) 1,4-phenylene, in which, optionally, one or two CH groups may be replaced by N, or
(c) a radical which is 1,4-cyclohexenylene, 1,3-cyclobutylene, 1,4-bicyclo(2,2,2)octylene, piperidine-1,4-diyl, naphthalene-2,6-diyl, decahydronaphthalene-2,6-diyl or 1,2,3,4-tetrahydronaphthalene-2,6-diyl,
where radicals (a) and (b) may be substituted by one CN or up to four fluorine,
A$^1$ can also be a single bond,
Z$^1$ is —CO—O—, —O—CO—, CH$_2$O—, —OCH$_2$—, —CH$_2$CH$_2$—, —CH=CH—, —C≡C— or a single bond, and
m is 1, 2 or 3.

2. A difluoromethylene compound of claim 1, wherein A$^1$ and A$^2$, independently are trans-1,4-cyclohexylene or 1,4-phenylene.

3. A difluoromethylene compound of claim 1, wherein Z$^1$ and Z$^2$, independently are —CH$_2$CH$_2$—, —C≡C— or a single bond.

4. A liquid-crystalline medium having at least two liquid-crystalline components, comprising at least one compound of claim 1.

5. In a liquid-crystal display element comprising a liquid crystal medium, the improvement wherein the liquid-crystalline medium is one of claim 4.

6. In an electrooptical display element comprising a liquid crystal dielectric, the improvement wherein the dielectric is a liquid-crystalline medium of claim 4.

7. A difluoromethylene compound according to claim 1 of the formulae Ia or Ib:

$$R^1-A^1-A^2-X-R^2 \quad \text{Ia}$$

$$R^1-A^1-Z^1-A^2-X-R^2 \quad \text{Ib}$$

wherein
X is S—CF$_2$.

8. A difluoromethylene compound according to claim 1 of the formulae $$R^1-A^1-A^1-A^2-X-R^2 \quad \text{Id}$$

$$R^1-A^1-Z^1-A^1-Z^1-A^2-X-R^2 \quad \text{Ie}$$

$$R^1-A^1-Z^1-A^1-A^2-X-R^2 \quad \text{If}$$

or $$R^1-A^1-A^1-Z^1-A^2-X-R^2 \quad \text{Ig}$$

wherein
X is S—CF$_2$.

9. A difluoromethylene compound according to claim 1 of the formulae $$R^1-A^1-A^1-A^1-A^2-X-R^2 \quad \text{Il}$$

$$R^1-A^1-Z^1-A^1-A^1-A^2-X-R^2 \quad \text{Im}$$

$$R^1-A^1-A^1-Z^1-A^1-A^2-X-R^2 \quad \text{In}$$

$$R^1-A^1-A^1-A^1-Z^1-A^2-X-R^2 \quad \text{Io}$$

$$R^1-A^1-Z^1-A^1-Z^1-A^1-A^2-X-R^2 \quad \text{Ip}$$

$$R^1-A^1-Z^1-A^1-A^1-Z^1-A^2-X-R^2 \quad \text{Iq}$$

$$R^1-A^1-A^1-Z^1-A^1-Z^1-A^2-X-R^2 \quad \text{Ir}$$

or $$R^1-A^1-Z^1-A^1-Z^1-A^1-Z^2-A^2-X-R^2 \quad \text{Is}$$

wherein
X is S—CF$_2$.

10. A difluoromethylene compound according to claim 7 of the formulae $$R^1-\text{Phe}-\text{Phe}-X-R^2 \quad \text{Iaa}$$

$$R^1-\text{Phe}-\text{Cyc}-X-R^2 \quad \text{Iab}$$

$$R^1-\text{Dio}-\text{Phe}-X-R^2 \quad \text{Iac}$$

$$R^1-\text{Pyr}-\text{Phe}-X-R^2 \quad \text{Iad}$$

$$R^1-\text{Pyd}-\text{Phe}-X-R^2 \quad \text{Iae}$$

$$R^1-\text{Cyc}-\text{Phe}-X-R^2 \quad \text{Iaf}$$

$$R^1-\text{Cyc}-\text{Cyc}-X-R^2 \quad \text{Iag}$$

or $$R^1-\text{Che}-\text{Phe}-X-R^2. \quad \text{Iah}$$

wherein
Phe is unsubstituted 1,4-phenylene or 1,4-phenylene which mono- or disubstituted by F or CN,
Cyc is 1,4-cyclohexylene,
Dio is 1,3-dioxane-2,5-diyl,
Pyd is pyridine-2,5-diyl,
Pyr is pyrimidine-2,5-diyl and
Che is 1,4-cyclohexenylene.

11. A difluoromethylene compound according to claim 7, of the formulae

R¹—Phe—CH₂CH₂—Phe—X—R²    Iba

R¹—Phe—OCH₂—Phe—X—R²    Ibb

R¹—Cyc—CH₂CH₂—Phe—X—R²    Ibc

R¹—Cyc—CH₂—CH₂—Cyc—X—R²    Ibd

R¹—Cyc—COO—Phe—X—R²    Ibe

R¹—Cyc—COO—Cyc—X—R²    Ibf

R¹—A¹—CH₂CH₂—Phe—X—R²    Ibg

R¹—A¹—CH₂CH₂—Cyc—X—R²    Ibh

R¹—A¹—CH₂O—Phe—X—R²    Ibi

R¹—A¹—OCH₂—Phe—X—R²    Ibj

R¹—A¹—COO—Phe—X—R²    Ibk

R¹—A¹—OCO—Phe—X—R²    Ibl or

R¹—Che—CH₂CH₂—Phe—X—R²    Ibm wherein
X is S—CF₂,
Phe is unsubstituted 1,4-phenylene or 1,4-phenylene which mono- or disubstituted by F or CN,
Cyc is 1,4-cyclohexylene,
Dio is 1,3-dioxane-2,5-diyl,
Pyd is pyridine-2,5-diyl,
Pyr is pyrimidine-2,5-diyl and
Che is 1,4-cyclohexenylene.

12. A difluoromethylene compound to claim 8 of the formulae

R¹—Phe—Phe—Phe—X—R²    Ida

R¹—Phe—Phe—Cyc—X—R²    Idb

R¹—Phe—Dio—Phe—X—R²    Idc

R¹—Cyc—Cyc—Phe—X—R²    Idd

R¹—Cyc—Cyc—Cyc—X—R²    Ide

R¹—Pyd—Phe—Phe—X—R²    Idf

R¹—Pyr—Phe—Phe—X—R²    Idg

R¹—Phe—Pyr—Phe—X—R²    Idh

R¹—Cyc—Phe—Phe—X—R²    Idi

R¹—Cyc—Phe—Cyc—X—R²    Idj

R¹—Dio—Phe—Phe—X—R²    Idk

R¹—Che—Phe—Phe—X—R²    Idl or

R¹—Phe—Che—Phe—X—R²    Idm wherein
X is S—CF₂,
Phe is unsubstituted 1,4-phenylene or 1,4-phenylene which mono- or disubstituted by F or CN,
Cyc is 1,4-cyclohexylene,
Dio is 1,3-dioxane-2,5-diyl,
Pyd is pyridine-2,5-diyl,
Pyr is pyrimidine-2,5diyl and
Che is 1,4-cyclohexenylene.

13. A difluoromethylene compound according to claim 7 in which
X—R is —S—CF₃.

14. A difluoromethylene compound according to claim 7 in which
X—R² is —S—CF₂—Cl.

15. A difluoromethylene compound according to claim 7 in which
X—R² is —S—CF₂—CN.

16. A difluoromethylene compound according to claim 1 of the formulae

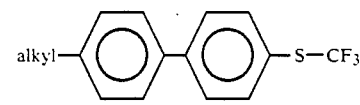   IIa

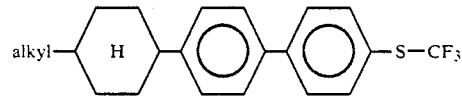   IIb

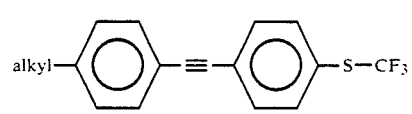   IIc

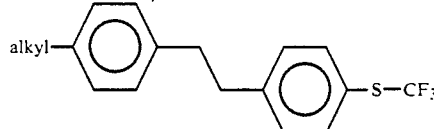   IId

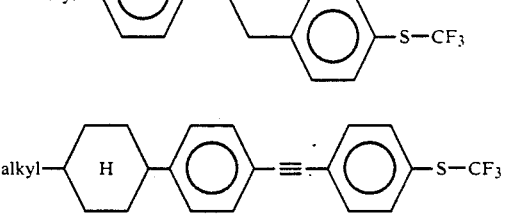   IIe

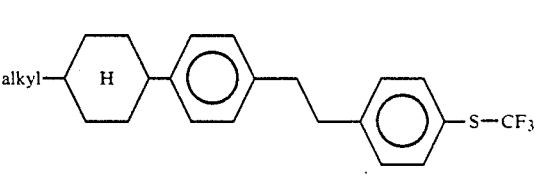   IIf

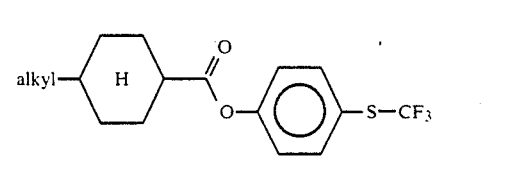   IIg

-continued
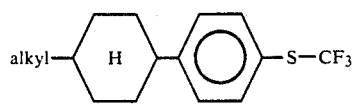
IIh
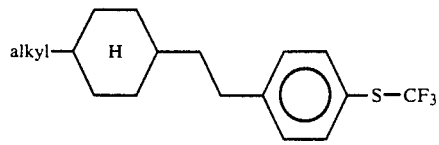
IIi
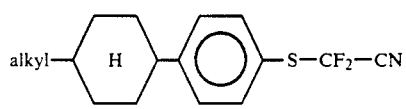
IIj
-continued
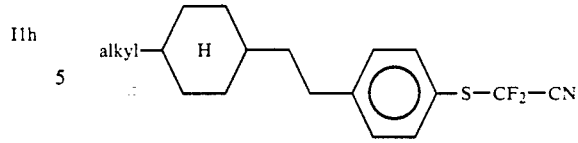
IIk
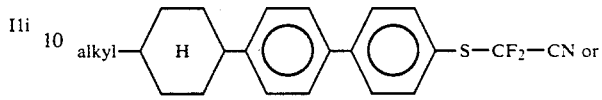
IIl
IIm
in which
alkyl- and alkoxy are in each case alkyl or alkoxy groups having 1 to 12 C atoms.
* * * * *